(12) United States Patent
Hill (10) Patent No.: US 9,445,781 B2
(45) Date of Patent: *Sep. 20, 2016

(54) LESION ASSESSMENT USING SIX DEGREE OF FREEDOM ULTRASOUND THERMOGRAPHY

(71) Applicant: St. Jude Medical, Atrial Fibrillation Division, Inc., St. Paul, MN (US)

(72) Inventor: Anthony D. Hill, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 43 days.

This patent is subject to a terminal disclaimer.

(21) Appl. No.: 14/584,779

(22) Filed: Dec. 29, 2014

(65) Prior Publication Data
US 2015/0201901 A1    Jul. 23, 2015

Related U.S. Application Data

(63) Continuation of application No. 14/363,683, filed as application No. PCT/US2012/071919 on Dec. 28, 2012, now Pat. No. 8,968,201.

(60) Provisional application No. 61/581,401, filed on Dec. 29, 2011.

(51) Int. Cl.
*A61B 8/08*    (2006.01)
*A61B 8/12*    (2006.01)
(Continued)

(52) U.S. Cl.
CPC ............... *A61B 8/12* (2013.01); *A61B 5/015* (2013.01); *A61B 8/4245* (2013.01); *A61B 8/445* (2013.01); *A61B 8/463* (2013.01); *A61B 8/5207* (2013.01);
(Continued)

(58) Field of Classification Search
CPC .... A61B 5/015; A61B 8/5223; A61B 8/587; A61B 5/0075; A61B 5/0084; A61B 5/6853
See application file for complete search history.

(56) References Cited

U.S. PATENT DOCUMENTS 7,806,829 B2    10/2010 Hauck
2003/0171691 A1*  9/2003 Casscells et al. ............. 600/549
(Continued)

FOREIGN PATENT DOCUMENTS

WO    2008/050276    5/2008

OTHER PUBLICATIONS

Seo, Chi Hyung et al., "The feasability of using thermal strain imaging to regulate energy delivery during intracardiac radio-frequency ablation", IEEE transactions on ultrasonics, ferroelectrics and frequency control, vol. 58, No. 7, pp. 1406-1417, Jul. 1, 2011.
(Continued)

*Primary Examiner* — Joel Lamprecht
(74) *Attorney, Agent, or Firm* — Dykema Gossett PLLC (57) ABSTRACT

A diagnostic device and method for assessing lesion formation by measuring temperature changes during endocardial ablation. Intracardiac echo catheter data is accurately mapped into a model maintained by a visualization, navigation, or mapping system using the position and orientation of the intracardiac echo catheter transducer within the model. For each point in the model, either a frequency shift or echo time shift is calculated from the intracardiac echo data to determine local temperature changes, and the local temperature changes are displayed within a rendering of the model for the user.

17 Claims, 5 Drawing Sheets

(51) Int. Cl.
*A61B 8/00* (2006.01)
*A61B 5/01* (2006.01)
*G01S 7/52* (2006.01)
*A61B 5/06* (2006.01)
*A61B 18/14* (2006.01)
*A61B 18/00* (2006.01)

(52) U.S. Cl.
CPC ......... *A61B 8/5223* (2013.01); *G01S 7/52036* (2013.01); *G01S 7/52071* (2013.01); *A61B 5/065* (2013.01); *A61B 8/4254* (2013.01); *A61B 18/14* (2013.01); *A61B 2018/00357* (2013.01); *A61B 2018/00577* (2013.01); *A61B 2018/00791* (2013.01)

(56) References Cited

U.S. PATENT DOCUMENTS

| | | |
|---|---|---|
| 2004/0127791 A1 | 7/2004 | Mast |
| 2007/0106157 A1* | 5/2007 | Kaczkowski et al. ........ 600/438 |
| 2008/0033417 A1 | 2/2008 | Nields |
| 2011/0087097 A1 | 4/2011 | Behar |
| 2011/0160593 A1 | 6/2011 | Deno et al. |
| 2014/0350400 A1* | 11/2014 | Hill .................... A61B 8/12 600/438 |

OTHER PUBLICATIONS

Seo, Chi Hyung et al., "Thermal strain imaging: a review", Physics in medicine and biology, vol. 1, pp. 649-664, May 23, 2011.

Stephens, Douglas N. et al., "Ultrasound compatible RF ablation electrode design for catheter based guidance of RF ablation—in vitro results with thermal strain imaging", Ultrasonics Symposium (IUS), pp. 229-232, Oct. 10, 2011.

Supplementary European Search Report in EP Application No. 12863284.1 (Mar. 31, 2015).

Title: International Search Report and Written Opinion Citation: PCT/US2012/071919 Publication Date: Mar. 12, 2013.

* cited by examiner

LESION ASSESSMENT USING SIX DEGREE OF FREEDOM ULTRASOUND THERMOGRAPHY

CROSS REFERENCE TO RELATED APPLICATIONS

This application is a continuation of U.S. application Ser. No. 14/363,683, filed 6 Jun. 2014 (the '683 application), now U.S. Pat. No. 8,968,201, issued on 3 Mar. 2015, which is a national stage application of International application no. PCT/US2012/071919, filed 28 Dec. 2012 (the '919 application), which claims the benefit of priority to U.S. application No. 61/581,401, filed 29 Dec. 2011 (the '401 application). The '683 application, '919 application, and '401 application are each hereby incorporated by reference as though fully set forth herein.

BACKGROUND OF THE INVENTION a. Field of the Invention

The present disclosure relates to monitoring of therapeutic procedures. In particular, the present disclosure relates to apparatus and methods for monitoring and displaying lesion formation during therapeutic procedures, such as cardiac ablation procedures utilized in the treatment of cardiac arrhythmia.

b. Background Art

It is well known that atrial fibrillation results from disorganized electrical activity in the heart muscle (the myocardium). The surgical maze procedure has been developed for treating atrial fibrillation, and involves the creation of a series of surgical incisions through the atrial myocardium in a preselected pattern so as to create conductive corridors of viable tissue bounded by scar tissue.

As an alternative to the surgical incisions of the maze procedure, transmural ablations of the heart may be used. Such ablations may be performed from within the chambers of the heart (endocardial ablation), using endovascular devices (e.g., catheters) introduced through arteries or veins. Various ablation techniques may be used, including, but not limited to, cryogenic ablation, radiofrequency ablation, laser ablation, ultrasonic ablation, and microwave ablation. The ablation devices are used to create elongated transmural lesions—that is, lesions extending through a sufficient thickness of the myocardium to block electrical conduction—forming the boundaries of the conductive corridors in the atrial myocardium. Perhaps most advantageous about the use of transmural ablation rather than surgical incision is the ability to perform ablation procedures without first establishing cardiopulmonary bypass (CPB).

Ablation devices are commonly used in conjunction with diagnostic systems that aid the practitioner in navigating, positioning and orienting the ablation device. These systems can provide a visual reference, such as a three dimensional model or two dimensional image, allowing the physician to more easily determine the orientation of the ablation device relative to the target anatomy. Intracardiac echo (ICE) catheters are one commonly used diagnostic tool that provides a two dimensional image of both therapeutic catheters and cardiac anatomy.

It is desirable for the practitioner (e.g., the doctor or electrophysiologist) to be able to monitor local temperature changes at the ablation site to allow the practitioner to more readily judge the extent of lesion formation during ablation procedures.

BRIEF SUMMARY OF THE INVENTION

The present disclosure, in one embodiment, describes a diagnostic system that utilizes an ICE catheter having an ultrasound transducer used to generate ultrasound echo data sets representing the reflected ultrasonic energy received by the transducer. The system also utilizes a visualization, navigation, or mapping (VNM) system configured to generate a model of the heart, track the position of the ultrasound transducer within the model, generate one or more temperature voxels within the model, and generate a two dimensional rendering of the model.

The VNM system is also configured to receive multiple ultrasound echo data sets and for each data set generate a mapped value by mapping at least a portion of the ultrasound echo data set onto a voxel element. The system further includes a display device configured to display a graphical user interface, and an electronic control unit (ECU) in communication with the intracardiac echo catheter, the VNM system, and the display device. The ECU is configured to receive the ultrasound echo data sets, the two dimensional rendering, and one or more user inputs directing the control of system components. The ECU is also configured to generate a graphic user interface containing the two dimensional rendering of the model as well as other display and control components.

The VNM system of the present embodiment generates a temperature value by comparing the mapped values from multiple ultrasound echo data sets. The system can determine temperature changes by determining a frequency shift or echo time shift between the mapped values of different ultrasound echo data sets. The voxels of the model can have a display value indicating the color in which the voxel is to be displayed in the two dimensional rendering, where the display value is representative of the temperature change for that voxel.

The ICE catheter of the system may also generate a temperature signal that can be used by the VNM system to generate an absolute temperature value when combined with the temperature change value. The ECU can also receive a temperature threshold as a user input that can be compared to the absolute temperature value, and the ECU can change the display value of a voxel when the absolute temperature of that voxel exceeds the threshold.

In another embodiment, the present disclosure describes a method of measuring temperature changes at a tissue treatment site comprising the steps of generating a model of the treatment area, locating at least one ICE catheter within the model, receiving an first ultrasound echo data set from the ICE catheter, and mapping the first ultrasound echo data set onto a plurality of voxel elements within the model. Then beginning treatment of the tissue, receiving a second ultrasound echo data set from the ICE catheter, mapping the second ultrasound echo data set onto a plurality of voxel elements within the model, and generating a temperature change value for each voxel element by comparing the mapped portion of the first ultrasound echo data set and the mapped portion of the second ultrasound data set. The method can determine the temperature change for each voxel by determining a frequency shift or an echo time shift from the mapped portion of the two echo data sets.

The method may also include a step that generates a two dimensional rendering of the model containing one or more of the voxel elements where the voxel elements are depicted using a color representative of the temperature change value. The method may also include the steps of receiving a temperature signal from the ICE catheter, and generating an absolute temperature value for each voxel element from the temperature change value for a given voxel and the temperature signal.

Where the method includes generating an absolute temperature value, the method may also include the step of generating a two dimensional rendering of the model containing one or more voxel elements where the voxel elements are depicted in a color representative of the absolute temperature value for each voxel element.

In yet another embodiment, the present disclosure describes a diagnostic device comprising an ECU in communication with an ICE catheter, a VNM system, and a display device. The ECU of the diagnostic device being configured to receive a plurality of ultrasound echo signals and a catheter position and orientation signal. The ECU is also configured to generate a model of a body cavity and locate the ICE catheter within the model using the catheter position and orientation signal. The model generated by the ECU can contain one or more voxel elements having a display value and a data value. The ECU of this embodiment is configured to generate a set of echo data elements from each received ultrasound echo signal where each echo data element is mapped onto one voxel element based on the catheter position and orientation signal. The ECU can generate a first echo data set and store the echo data elements as the data value of the corresponding voxel elements. The ECU can then generate a second set of echo data elements and map each echo data element from the second set onto a voxel. For each voxel having a data element from both data sets mapped onto it, the ECU can generate a display value representing a temperature change for the voxel using the data value and the mapped second data element.

In this embodiment, the temperature change can be generated by determining a frequency shift or echo time shift between the data value and the second data element for each voxel. The ECU can also be configured to generate a two dimensional rendering of the model containing one or more voxel elements where the voxel elements are depicted in a color representative of the display value of each voxel.

The ECU of this embodiment can also be configured to receive a temperature signal and generate an absolute temperature value from the display value and the temperature signal. Where the ECU generates an absolute temperature signal, the ECU can be configured to generate a two dimensional rendering of the model containing one or more voxel elements, the voxel elements being depicted in a color representative of the absolute temperature value. Where the ECU generates an absolute temperature signal, the ECU may also be configured to receive a user input indicating a temperature threshold, where the ECU will generate a two dimensional rendering depicting the voxel elements having an absolute temperature value less than the temperature threshold using a color representative of the absolute temperature value and the voxel elements having an absolute temperature equal to or greater than the temperature threshold using an alert color.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
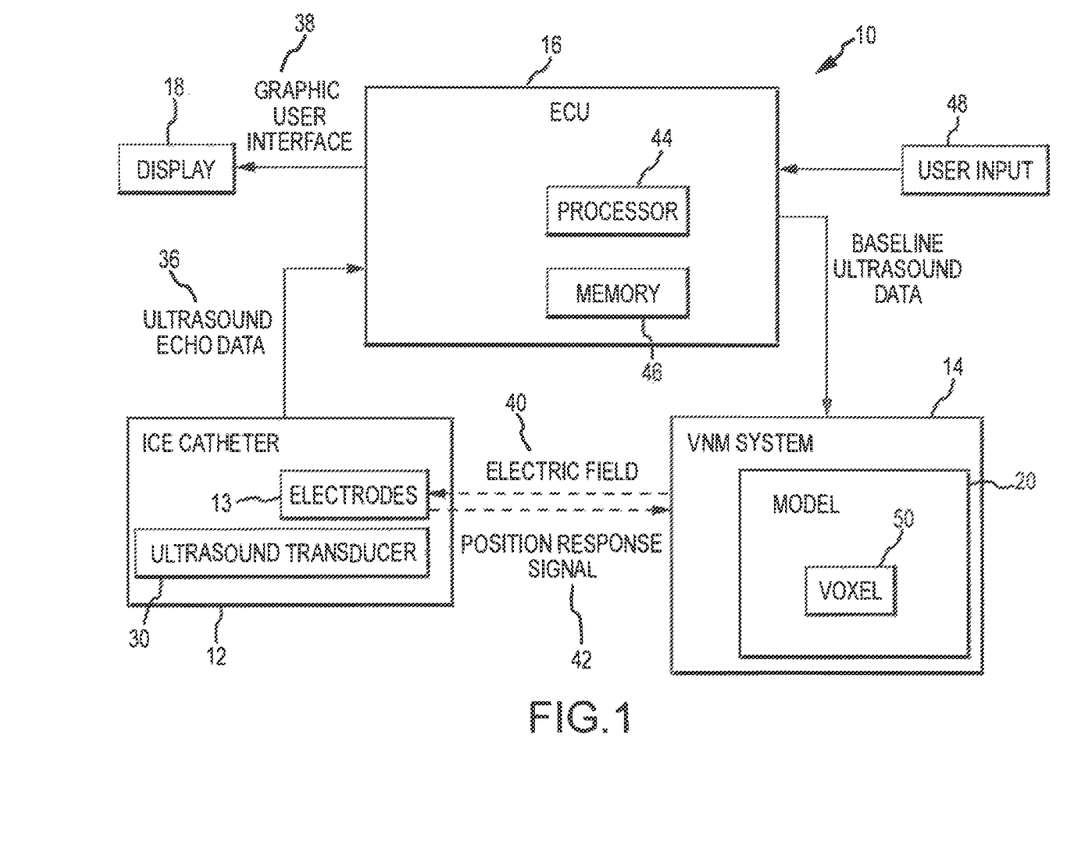
FIG. 1 is a block diagram illustrating the operation of the system of the present disclosure prior to the start of a therapeutic treatment.
Figure 2:
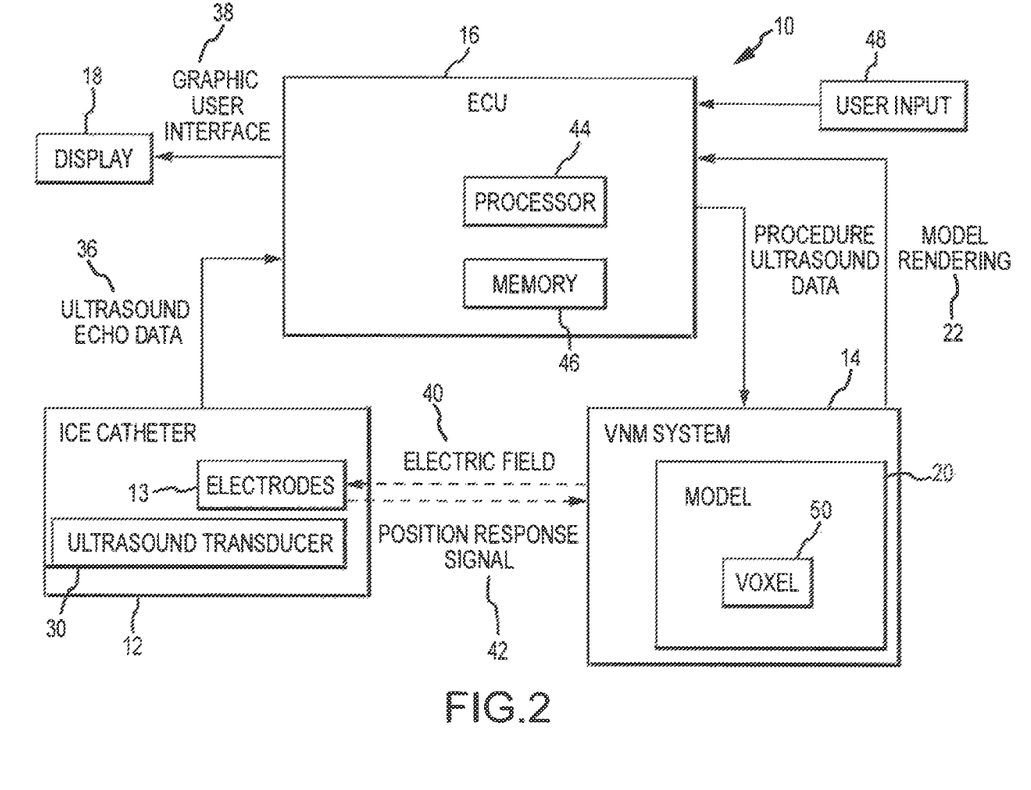
FIG. 2 is a block diagram illustrating the operation of the system of the present disclosure after the beginning of a therapeutic treatment.

Referring now to the drawings wherein like reference numerals are used to identify identical components in the various views, FIGS. 1 and 2 are block diagrams illustrating the relationship between the elements of the system of the present disclosure.

The present disclosure provides a diagnostic system 10 capable of monitoring lesion formation during ablation. The diagnostic system includes an ICE catheter 12 containing one or more electrodes 13, an anatomical visualization, navigation, and mapping system ("VNM system") 14, an electronic control unit ("ECU") 16, and one or more display devices 18. The VNM system 14 is used to detect therapeutic and diagnostic devices within the body and locate the devices within a model 20 of the heart and surrounding vasculature. The VNM system 14 can track detected therapeutic and diagnostic devices as they move within the heart and update their locations in the model 20 such that the model 20 is updated in substantially real time. The VNM system can create a two dimensional rendering 22 of the model 20 depicting the position and orientation ("P&O") of the devices within the model 20, which may be used as part of a graphic user interface depicted on the display 18. When the VNM system 14 is used to display the P&O of an ICE catheter 12 within the heart, the echo plane of the ICE catheter 12 can be mapped within the model 20. Displaying the P&O of the ICE catheter 12 and its echo plane allows a physician to more easily navigate an ICE catheter 12 and thereby create an ICE image of a desired anatomical feature, such as an ablation target site. During the ablation procedure, the echo plane of the ICE catheter 12 can be used to estimate lesion formation by detecting temperature changes at the ablation site.

Figure 3:
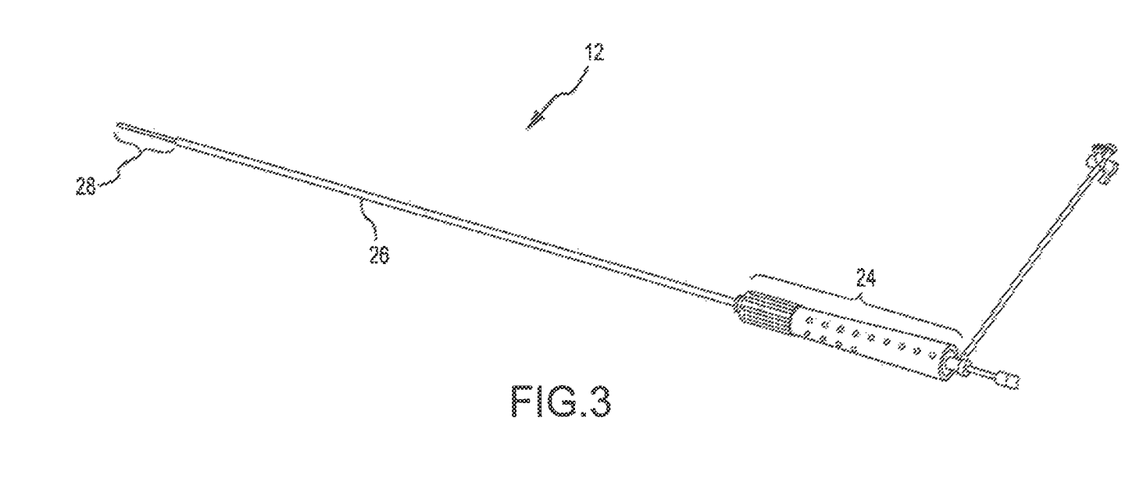
FIG. 3 depicts an example of an intracardiac echo catheter suitable for use in the system of the present disclosure.
Figure 4:
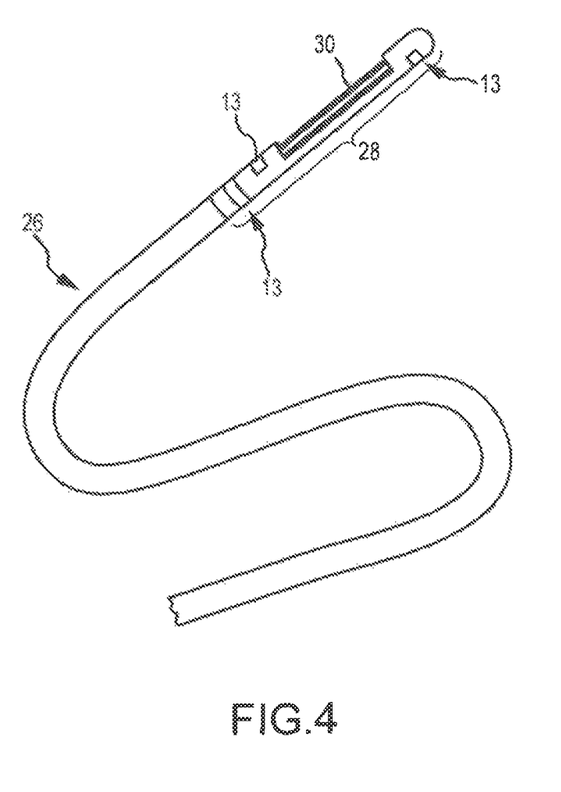
FIG. 4 depicts an example of the distal end of an echo catheter suitable for use in the system of the present disclosure.

Referring now to FIGS. 3 and 4, which illustrate an example of an ICE catheter for use in the system of the present disclosure.

ICE Catheter

The ICE catheter 12 may comprise a control handle 24, a long flexible body member 26, and a sensor array 28 containing an ultrasound sensor 30 and a plurality of electrodes 13. The sensor array 28 is fixed to the end of the flexible body member 26 and may be inserted intravenously and navigated to the heart by manipulating the length of the flexible body member 26 using the control handle 24.

Figure 5A:
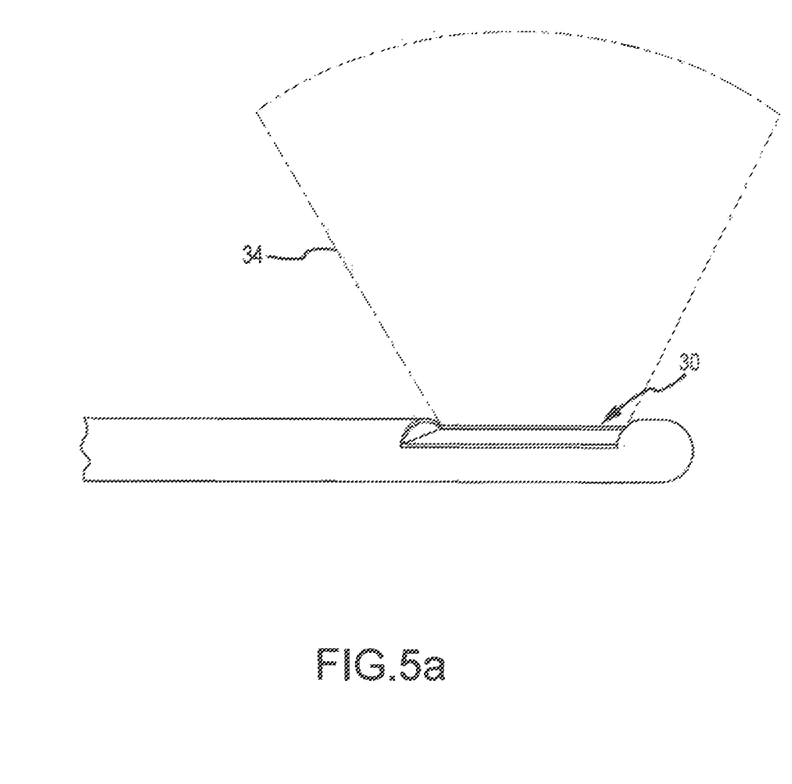
FIG. 5a is a schematic view of the ultrasound transducer illustrating the plane of emitted ultrasonic energy.
Figure 5B:
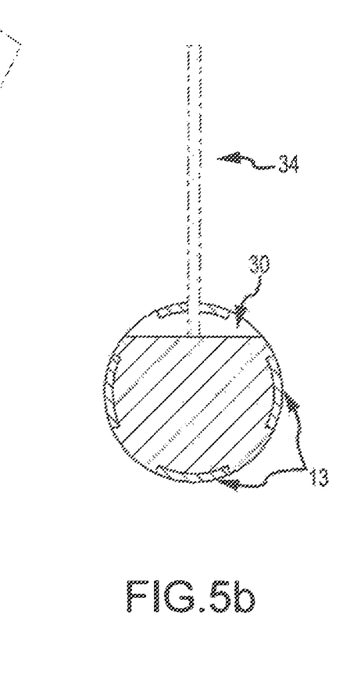
FIG. 5b is a cross sectional view of the ultrasound transducer illustrating the plane of emitted ultrasonic energy.

As depicted in FIGS. 5a and 5b, the ultrasound transducer 30 emits ultrasonic energy pulses in a generally fan shaped echo plane 34, and receives echo pulses when the ultrasonic energy is reflected back to the transducer 30 by a scattering object intersected by a pulse in the echo plane 34. The transducer 30 produces ultrasound echo data 36 (shown in FIG. 2) representative of the received echo pulses that can be used to create an ICE image depicting objects located within the echo plane 34. The ultrasound echo data 36 can be unprocessed ultrasound transducer signals, or may be conditioned using one or more amplification and filtering circuits, such as, by way of example, backscatter A-line data.

ICE images may be gray scale images with tissue structures, catheters and other dense objects being displayed in white, while dark portions of the image tend to represent cavity space filled with fluid. The more echogenic (e.g., the denser) a material is, the brighter its representation will be displayed in the image. The image can be generated by the ICE catheter 12, or by the ECU 16 of the system after receiving the ultrasound echo data from the ultrasound transducer 30. For purposes of clarity and illustration only, the description below will be limited to an embodiment having the ICE image created by the ECU 16.

Referring now back to FIGS. 1 and 2, the ICE image generated by ECU 16 can be incorporated into a graphic user interface 38. The graphic user interface 38 is displayed on one or more of the display devices 18 of the system 10. In an alternative embodiment, the ICE image can be incorporated into the graphic user interface 38 such that the ICE image appears projected within the two dimensional rendering 22 of the model 20 maintained by the VNM system 14. Display of the ICE image within the rendering 22 of the model 20 allows a physician to more easily correlate features within the ICE image to anatomical features in the model 20.

The plurality of electrodes 13 or other sensors configured to be responsive to the VNM system 14 allow the system 10 to determine the P&O of the ICE catheter 12 within the model 20. The ICE catheter 12 is electrically coupled to the ECU 16 and may contain three or more electrodes 13 responsive to an electric field 40 (shown in FIGS. 1 and 2) generated by the VNM system 14. The electrodes 13 being configured to generate a position response signal 42 when positioned within an electric field 40 generated by the VNM system 14. The position response signal 42 may be received directly by the VNM system 14 or may be communicated to the VNM system 14 through the ECU 16. The electrodes 13 can be positioned within the sensor array 28 such that the VNM system 14 may determine the P&O of the ultrasound sensor 30 with six degrees of freedom in the model 20 maintained by the VNM system 14, thereby allowing the ICE image to be located within the model 20.

In an alternative embodiment, one or more electrodes 13 may be replaced with magnetic sensors responsive to a magnetic field generated by the VNM system 14. An example of such an ICE catheter 12 is described in copending U.S. patent application Ser. No. 12/982,968 filed Dec. 31, 2010 entitled "INTRACARDIAC IMAGING SYSTEM UTILIZING A MULTIPURPOSE CATHETER," which is hereby incorporated by reference in its entirety as though fully set forth herein.

VNM System

The ECU 16 is electrically coupled to (i.e., via wires or wirelessly) to the VNM system 14, which generates and maintains the model 20 of the heart and surrounding vasculature or other body structure. The VNM system 14 may further be configured to allow the user to identify features within the model 20 and include the location as well as other information associated with the identified feature, such as an identifying label. By way of example, identified features may include ablation lesion markers or anatomical features such as cardiac valves.

The VNM system 14 functionality may be provided as part of a larger visualization, navigation, or mapping system, for example, an ENSITE™ VELOCITY™ system running a version of ENSITE™ NAVX™ software commercially available from St. Jude Medical, Inc., and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present application, and hereby incorporated by reference in its entirety.

The VNM system 14 may comprise conventional apparatus known generally in the art, for example, the ENSITE™ VELOCITY™ system described above or other known technologies for locating/navigating a catheter in space (and for visualization), including for example, the CARTO™ visualization and location system of Biosense Webster, Inc., (e.g., as exemplified by U.S. Pat. No. 6,690,963 entitled "SYSTEM FOR DETERMINING THE LOCATION AND ORIENTATION OF AN INVASIVE MEDICAL INSTRUMENT" hereby incorporated by reference in its entirety), the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3™ visualization and location system of Biosense Webster, Inc. (e.g., as exemplified by U.S. Pat. No. 7,536,218, and 7,848,789 both of which are hereby incorporated by reference in its entirety).

Some of the localization, navigation and/or visualization systems may involve providing a sensor for producing signals indicative of catheter location and/or orientation information, and may include, for example one or more electrodes 13 in the case of an impedance-based localization system such as the ENSITE™ VELOCITY™ system running ENSITE™ NAVX™ software, which electrodes may already exist in some instances, or alternatively, one or more coils (i.e., wire windings) configured to detect one or more characteristics of a low-strength magnetic field, for example, in the case of a magnetic-field based localization system such as the gMPS system using technology from MediGuide Ltd. described above.

Although the exemplary VNM systems 14 described above each maintain a model 20 of the body cavity, acceptable alternative mapping devices for creating a model of cardiac structures include magnetic resonance imaging (MR) and x-ray computed tomography (CT).

While each of the electric-impedance, magnetic field, and hybrid magnetic field-impedance based systems disclosed above can act as the VNM system 14 and remain within the scope and spirit of the present disclosure, the VNM system 14 of the remaining discussion will be assumed to be an impedance based system for the purposes of clarity and illustration unless otherwise noted.

ECU

Referring now to FIGS. 1 and 2 depicting a block diagram of embodiments of the present invention, the ECU 16 will be discussed. The ECU 16 may include a programmed electronic controller having a processor 44 in communication with a memory 46 or other computer readable media (memory) suitable for information storage. Relevant to the present disclosure, the ECU 16 is configured, among other things, to receive user input 48 from one or more user input devices electrically connected to the system 10 and to issue commands (i.e., display commands) to the display devices 18 attached to the system 10 directing the depiction of the graphic user interface 38. The ECU 16 may be configured to be in communication with the ICE catheter 12 and the VNM system 14 to facilitate the creation of a graphic user interface 38 containing at least an ICE image, a two dimensional rendering 22 of the model 20, or both. The communication between the ICE catheter 12, the ECU 16, and the VNM system 14 may be accomplished in an embodiment through a communications network (e.g., a local area network or the internet) or a data bus.

It should be understood that although the VNM system 14, the ICE catheter 12, and the ECU 16 are shown separately, integration of one or more computing functions may result in a system including an ECU 16 on which may be run both (i) various control and image formation functions of the ICE catheter 12 and (ii) the modeling and position tracking functionality of the VNM system 14. For purposes of clarity and illustration only, the description below will be limited to an embodiment having the modeling and position tracking functionality of the VNM system 14 separate from the ECU 16.

Frequency Shift Temperature Estimation

In addition to generating an ICE image, the ICE catheter 12 may be used to estimate lesion formation during an ablation procedure. By positioning the ultrasound transducer 30 such that the echo plane 34 intersects the ablation target site, changes in temperature at the site can be detected by measuring local frequency shifts or echo time shifts in the reflected ultrasound echo data 36. Detected temperature changes may be visualized using a plurality of temperature voxels 50 within the model 20 at the ablation target site. The system 10 allows local temperature changes to be detected despite the movement of the ICE catheter, the target anatomy—i.e., beating of the patient's heart, or a combination of the two—by mapping received ultrasound echo data 36 into the model 20. Mapping data into the model allows the ECU 16 to compare discrete ultrasound echo data points from the same tissue structures to determine a relative temperature change for each point. As the relative temperature changes are determined, the display values for each corresponding voxel 50 can be changed to reflect the new temperature change thereby causing the two dimensional rendering 22 to be updated accordingly.

In one embodiment of the system 10 of the present disclosure, the local temperature changes at the ablation site are determined using the ultrasound echo data 36 by measuring frequency shifts in the ultrasound backscatter A-line data as described in detail in Noninvasive Estimation of Tissue Temperature Responsive to Heating Fields Using Diagnostic Ultrasound, Seip, Ebbini, IEEE Transactions on Biomedical Engineering, Vol. 42, No. 8, August 1995, which is hereby incorporated by reference in its entirety. The frequency shift method computes a detailed autoregressive power spectrum from the A-line data generated by the ICE catheter 12 to model detected frequency shifts as tissue temperature changes. The frequency shift depends on the effect of a temperature change on two variables, the first being the average scatter spacing d in the tissue and the second being the speed of sound c in the tissue, which can be expressed as:

$$f_k(T) = \frac{kc(T)}{2d(T)} \quad k = 1, 2, 3, \ldots, \infty. \tag{1}$$

where k is the harmonic of the fundamental frequency, c(T) is the speed of sound in the medium as a function of temperature T, and d(T) is the average scatter spacing as a function of temperature.

The average scatter spacing d of a tissue increases as the temperature increases and decreases as the temperature decreases. This increase and decrease of d as a function of temperature is determined by the linear coefficient of thermal expansion α of the tissue or medium in general. The average scatter spacing d as a function of temperature is approximately given by:

$$d = d_0(1 + \alpha \Delta T) \tag{2}$$

where α is the linear coefficient of thermal expansion of the medium and $d_0$ is the average scatter spacing at a baseline temperature $T_0$.

The speed of sound c increases with increasing temperature in most tissues, including muscle and other tissues containing mostly water, but decreases with increasing temperature in fatty tissues. By differentiating (1) with respect to time T and using (2) within the result yields an expression for approximating a frequency shift $\Delta f_k$ as function of temperature:

$$\Delta f_k(T) \approx \frac{k}{2d_0}\left[\frac{\partial c(T)}{\partial T}\bigg|_{T=T_0} - \alpha c_0\right]\Delta T \tag{3}$$

where $c_0$ is the value of the speed of sound in the medium at the baseline temperature of $T_0$. As can be seen in (3), a frequency shift detected in the ICE catheter 12 A-line data can be used to approximate a temperature change when the linear coefficient of thermal expansion α and the temperature dependence of the speed of sound in the medium $$\frac{\partial c(T)}{\partial T}$$

are known.

Eco Time-Shift Temperature Estimation

In another embodiment of the system of the present disclosure, the local temperature changes at the ablation site are determined using the ultrasound echo data 36 by measuring echo time-shifts of ultrasound scatter locations in A-line data as described in detail in Two-Dimensional Temperature Estimation Using Diagnostic Ultrasound, Simon, VanBaren, Ebbini, IEEE Transactions on Ultrasonics, Ferroelectrics, and Frequency Control, Vol. 45, No. 4, July 1998, which is hereby incorporated by reference in its entirety.

The thermal dependence of ultrasound echo time-shift is related to changes in the speed of sound in the medium and to thermal expansion of the medium. The former produces an apparent shift in scatter location, while the latter produces a physical shift. The observed time shift for an echo from a scatterer at an axial depth z can be described as:

$$\Delta t(z) = t(z) - t(z_0) = 2\int_0^z \left[\frac{1 + \alpha(d)\Delta T(d)}{c(d, T(d))} - \frac{1}{c(d, T_0)}\right]\partial d \tag{4}$$

where α(d) is the linear coefficient of thermal expansion of the medium, at depth d, ΔT(d) is the change in temperature at depth d, and c(d,T(d)) and c(d,$T_0$) are the speed of sound at depth d at temperature T and an initial temperature $T_0$, respectively. Differentiating (4) and substituting for the case where the thermal dependence on the speed of sound in tissue is approximately linear, as is the case with ablation temperatures, yields an expression for the change in temperature as a function of the time shift.

$$\Delta T(z) = \frac{c_0(z)}{2}\left(\frac{1}{\alpha(z)-\beta(z)}\right)\frac{\partial}{\partial z}(\Delta t(z)) \quad (5)$$

where $$\beta(z) = \frac{1}{c_0(z)} \cdot \frac{\partial c(z, T)}{\partial T}\bigg|_{T=T0} \text{ and } c_0(z) = c(z, T_0).$$

When the speed of sound in the medium and the coefficient of thermal expansion are invariant with respect to depth, then $c_0(z)=c_0$, $\alpha(z)=\alpha$, and $\beta(z)=\beta$.

The algorithm for estimating temperature in a two dimensional plane requires tracking the cumulative echo time-shift $\partial t(z,x,T_i)$ at each location and time $T_i$, and then differentiating it along the axial direction (z) and filtering both axial and lateral (x) directions. The symbol $T_i$ represents the time at which each ith frame was acquired, not the echo time delays t. The temperature estimation algorithm can be accomplished by the following steps:

1) Acquiring two dimensional echo data from the ICE catheter 12 prior to any heating of the target anatomy to establish a base line temperature $r(z,x,T_0)$, i=0;
2) Start heating, i.e., by beginning the ablation treatment at the target site;
3) Acquiring another two dimensional echo data reading $r(z,x,T_i)$, i=i+1;
4) Estimating the incremental time-shift map;

$$\partial \hat{t}_{incr}(z,x,T_i) = \hat{t}(z,x,T_i) - \hat{t}(z,x,T_{i-1}) \quad (6)$$

at time $T_i$ using the current and previous frames $r(z,x,T_i)$ and $r(z,x,T_{i-1})$;
5) Computing the cumulative time-shift map;

$$\partial \hat{t}(z, x, T_i) = \sum_{k=1}^{i} \partial \hat{t}_{incr}(z, x, T_k) \quad (7)$$

6) Differentiating the cumulative time-shift map $\partial \hat{t}(z,x,T_i)$ along the axial direction and filtering along the axial and lateral directions, using a two dimensional separable FIR filter;
7) Scaling the results of the sixth step by $kc_0/2$ to obtain the temperature-change map estimates $\partial \hat{\theta}(z,x,T_i)$ at time $T_i$; and
8) Returning to step three and repeating until all of the desired two dimensional echo data has been acquired.

The incremental time shifts can be very small and are commonly less than the echo sampling period. In order to obtain accurate incremental time-shifts in the echo sub-sample range an auto-correlation technique can be utilized to allow the incremental time-shift to be estimated from the phase of the axial component of a 2-D complex auto-correlation of two subsequent frames of echo data 36. The first step in of the auto-correlation function is to compute the analytic signal of the echo data using an FIR Hilbert Transformer h(m). The 1-D discrete time Hilbert transform of the echo signal along the axial direction can be obtained by convolusion of the discrete time sampled echo data and the Hilbert Transformer h(m), given by:

$$\tilde{r}(m,n,s) = r(m,n,s) * h(m) \quad (8)$$

where r(m,n,s) is the discrete-time sampled echo data, where m is the index along the axial direction, n is the index along the lateral direction, and s is the frame index (wall clock time). An analytic signal can be obtained using (8) through:

$$\hat{r}(m,n,s) = r(m,n,s) - j\tilde{r}(m,n,s). \quad (9)$$

When using an echo image consisting of M samples along the axial direction and N samples along the lateral direction, the q-th lag, along the axial direction of the complex auto-correlation function at location (m, n) and time s is defined as:

$$\hat{\gamma}(m, n; q, 0) = \quad (10)$$

$$\sum_{m'=-\frac{M}{2}}^{\frac{M}{2}-1} \sum_{n'=-\frac{N}{2}}^{\frac{N}{2}-1} \hat{r}(m+m', n+n', s-1) \cdot \hat{r}^*(m+m'+q, n+n', s)$$

where the superscript * denotes complex conjugation, and M and N are assumed to be even numbers for simplicity. From (10) the incremental time-shifts smaller than the sampling period can be estimated from the phase of the auto-correlation function computed at lags q=−1, q=0 and q=1 using:

$$\Delta \hat{t}(m, n) = \frac{2 \angle \hat{\gamma}(m, n; 0, 0)}{\angle \hat{\gamma}(m, n; 1, 0) - \angle \hat{\gamma}(m, n; 1, 0)} t_{sp}, \quad (11)$$

where $t_{sp}$ is the time for one sampling period of the RF-echo, and $\angle$ is the angle operator. Estimates of $\Delta \hat{t}(m,n)$ can be truncated to the range $[-t_{sp}, t_{sp}]$ to avoid outliers when time-shift increments are smaller than $t_{sp}$.

The frequency domain and echo time-shift methods have been previously used with in relatively static configurations where neither the target tissue nor the ultrasound transducer is subject to appreciable movement during the temperature estimation procedure. When movement is introduced into the environment it becomes difficult to map newly received ultrasound echo data to allow an accurate comparison with existing echo ultrasound data.

An accurate comparison between the two data sets is difficult because when the ICE catheter and the target tissue move relative to one another or the orientation of the ICE catheter changes relative to the target tissue the ultrasound echo data from the new position or orientation cannot be directly compared to data from the prior position or orientation without having known spatial relationship between the earlier and later data. Without a system for tracking the ICE catheter's position in the heart there is no known relationship between the temporally distinct ultrasound echo data sets, which makes it very difficult to produce accurate temperature determinations when movement occurs. This static configuration limitation has previously rendered these temperature estimation techniques inappropriate for dynamic environments such as the atrial chambers of the heart or other active muscle systems.

The system of the present disclosure allows these temperature estimation techniques to be extended to dynamic environments through the interaction of the ICE catheter and VNM system when gathering the ultrasound echo data used in either temperature estimation algorithm.

The VNM system 14 enables temperature estimation in a dynamic environment by tracking the movements of the ICE catheter 12 within the heart, which allows the system to accurately map received ultrasound echo data 36 into the model 20 of the VNM system 14. Using the P&O of the ICE catheter 12, determined by the VNM system 14, each frame of received ultrasound echo data 36 can be mapped into the model 20 using voxel elements 50 to represent the tissue temperatures.

As features in the cardiac or other therapeutic environment move, such as the contraction of the cardiac chamber or movement of the ICE catheter 12 within the cardiac chamber, the ultrasound echo data 36 can be associated with the then existing P&O of the ICE catheter 12 and from that point be accurately mapped into the model 20. Thus, the model 20 and the ICE catheter's 12 known position in the model 20 at all times provides a known spatial relationship between any two temporally distinct set of ultrasound echo data 36 received by the ICE catheter 12. When ultrasound echo data 36 from multiple echo frames are mapped into the same voxel 50 the data 36 from previous echo frames can be used with the newly mapped frame to generate an estimated temperature change using one of the methods previously discussed.

Now referring back to FIGS. 1 and 2, to accurately estimate temperature changes attributable to a therapeutic procedure, a baseline or background ultrasound echo data set 36 for the target anatomy should be mapped into the model 20. The baseline echo data 36 can be gathered by the user while using the ICE catheter 12 to aid in navigating the therapeutic catheter into position, or when creating echo images of the target anatomy and surrounding tissue prior to ablation.

Once the baseline echo data 36 has been mapped into the voxels 50 within the model 20, data gathered during the therapeutic procedure can be used to generate temperature change estimates associated with the procedure. As the echo data 36 is mapped into the voxels 50 within the model 20, the display of the voxels 50 can be changed so as to create a visual reference of temperature at the therapeutic site. One such visual reference is a heat map, where the base line temperature is depicted as a green or blue color and, as the estimated temperature change of a voxel rises, its display color progresses along the visible light spectrum, with red representing the highest temperature change. A relative temperature change computed by the ECU 16 may be combined with temperature data from other temperature sensors present in the cardiac environment to generate an absolute temperature estimation for each voxel element 50.

Varying the display of the voxel elements 50 from a minimum baseline temperature to a maximum temperature set by the desired therapeutic temperature allows a user to easily determine which portions of the target anatomy have reached the desired therapeutic temperature. In one embodiment of the system 10 a voxel's 50 display color can be changed to one not normally within the range of heat map temperatures, such as a violet or purple color, making it more distinct from the surrounding tissue.

Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for assessing a lesion at a tissue treatment site, comprising:
   determining a first position and first orientation of a catheter equipped with ultrasound, based on a first signal received from a position sensor disposed on the catheter;
   collecting a first set of echo data from the catheter equipped with ultrasound at the first position and first orientation, wherein the first set of echo data is associated with the tissue treatment site;
   determining a second position and second orientation of the catheter equipped with ultrasound, based on a second signal received from the position sensor disposed on the catheter;
   collecting a second set of echo data from the catheter equipped with ultrasound at the second position and second orientation, wherein the second set of echo data is associated with the tissue treatment site;
   associating the first and second set of echo data with the tissue treatment site based on the first and second signal received from the position sensor, respectively;
   determining a first temperature of the tissue treatment site from the first set of echo data and a second temperature of the tissue treatment site from the second set of echo data; and
   assessing, with a computer, a formation of the lesion based at least in part on a difference between the first and second temperatures exceeding a threshold.

2. The method of claim 1, wherein:
   the first position and first orientation of the catheter equipped with ultrasound is associated with a first time; and
   the second position and second orientation of the catheter equipped with ultrasound is associated with a second time, different than the first time.

3. The method of claim 2, wherein the first set of echo data is associated with the first time and the second set of echo data is associated with the second time.

4. The method of claim 2, wherein at least one of the position and orientation of the catheter changes between the first time and the second time.

5. The method of claim 1, wherein assessing the lesion based at least in part on the difference between the first and second temperatures comprises determining a frequency shift between the first set of echo data and the second set of echo data.

6. The method of claim 1, wherein assessing the lesion based at least in part on the difference between the first and second temperatures comprises determining an echo time shift between the first set of echo data and the second set of echo data.

7. The method of claim 1, further comprising generating a model of a treatment area that includes the tissue treatment site.

8. The method of claim 7, further comprising:
   displaying a change between the first temperature and the second temperature on the model; and displaying the first position and first orientation of the catheter and the second position and second orientation of the catheter on the model.

9. A system for assessing a lesion at a tissue treatment site, the system comprising a processor and a memory storing instructions executable by the processor to:
receive a first ultrasound echo data set associated with a treatment site from an intracardiac echo catheter;
receive a second ultrasound echo data set associated with the treatment site from the intracardiac echo catheter;
generate a model of the treatment site;
map the first and second ultrasound echo data set onto at least one voxel element in the model of the treatment site;
determine a first temperature of the treatment site from the first ultrasound echo data set;
determine a second temperature of the treatment site from the second ultrasound echo data set; and
assess a formation of the lesion based at least in part on a difference between the first and second temperatures exceeding a threshold.

10. The system of claim 9, further comprising instructions executable by the processor to determine a change between the first temperature of the treatment site and the second temperature of the treatment site.

11. The system of claim 10, further comprising instructions executable by the processor to determine an absolute temperature value for the change between the first temperature and the second temperature.

12. The system of claim 11, wherein a display value of the at least one voxel is changed in response to the absolute temperature exceeding a threshold value.

13. The method of claim 9, wherein the instructions executable to assess the lesion based at least in part on the difference between the first and second temperatures further comprise instructions executable to:
determine a frequency shift between the first set of echo data and the second set of echo data; and
determine an echo time shift between the first set of echo data and the second set of echo data.

14. The system of claim 9, wherein:
the first ultrasound echo data set is associated with a first position and orientation of the intracardiac echo catheter; and
the second ultrasound echo data set is associated with a second position and orientation of the intracardiac echo catheter.

15. A non-transitory computer readable medium comprising instructions for assessing a lesion, the instructions executable by a processor to:
generate a model of a treatment area that includes a treatment site;
receive a first ultrasound echo data set associated with the treatment site from an intracardiac echo catheter;
receive a second ultrasound echo data set associated with the treatment site from the intracardiac echo catheter;
map the first ultrasound echo data set onto at least one voxel element in the model of the treatment site;
map the second ultrasound echo data set onto the at least one voxel element in the model of the treatment site;
determine a first temperature of the treatment site from the first ultrasound echo data set;
determine a second temperature of the treatment site from the second ultrasound echo data set; and
assess a formation of the lesion based at least in part on a difference between the first temperature and the second temperature exceeding a threshold.

16. The non-transitory computer readable medium of claim 15, further comprising instructions executable to display the intracardiac echo catheter on the model.

17. The non-transitory computer readable medium of claim 15, further comprising instructions executable to generate a temperature change value for each of the at least one voxel element by comparing the mapped portion of the first ultrasound echo data set and the mapped portion of the second ultrasound echo data set.

* * * * *